(12) United States Patent
Cheng

(10) Patent No.: US 9,504,810 B2
(45) Date of Patent: Nov. 29, 2016

(54) DEVICE FOR DRAINING LYMPH INTO VEIN

(71) Applicant: Ming-Huei Cheng, Taipei (TW)

(72) Inventor: Ming-Huei Cheng, Taipei (TW)

( * ) Notice: Subject to any disclaimer, the term of this patent is extended or adjusted under 35 U.S.C. 154(b) by 228 days.

(21) Appl. No.: 14/017,798

(22) Filed: Sep. 4, 2013

(65) Prior Publication Data

US 2014/0155806 A1 Jun. 5, 2014

(30) Foreign Application Priority Data

Dec. 5, 2012 (TW) .............................. 101145604 A

(51) Int. Cl.
*A61M 5/00* (2006.01)
*A61M 27/00* (2006.01)
*A61M 5/165* (2006.01)
*A61F 2/01* (2006.01)

(52) U.S. Cl.
CPC ........... *A61M 27/002* (2013.01); *A61M 5/165* (2013.01); *A61F 2/01* (2013.01); *A61M 2202/0028* (2013.01); *A61M 2202/0405* (2013.01)

(58) Field of Classification Search
CPC ............. A61M 27/002; A61M 5/165; A61M 2202/0028; A61M 2202/0405; A61F 2/01
USPC ....................................... 604/8, 9
See application file for complete search history.

(56) References Cited

U.S. PATENT DOCUMENTS

| 5,476,445 A * | 12/1995 | Baerveldt et al. ................. 604/8 |
| 2007/0156079 A1* | 7/2007 | Brown ............................... 604/9 |
| 2011/0208319 A1* | 8/2011 | Laster ................. A61M 1/1678 623/23.65 |
| 2014/0114227 A1* | 4/2014 | Zamarripa et al. ............... 604/8 |

FOREIGN PATENT DOCUMENTS

WO WO 2014015377 A1 * 1/2014

* cited by examiner

*Primary Examiner* — Leslie Deak
(74) *Attorney, Agent, or Firm* — Muncy, Geissler, Olds & Lowe, P.C.

(57) ABSTRACT

The present invention relates to a device for draining lymph into vein, which comprises: a storage chamber including a chamber wall, wherein a storage space formed by the chamber wall, and at least one first opening and a second opening are formed on the chamber wall; at least one osmosis membrane disposed at the first opening so that lymph can penetrate into the storage space, wherein the osmosis membrane is made of negative charged polymer molecules; a first conduit, of which one end connects to the storage space, and the other end connects with a vein so that the space can connect with the vein; and a pump provided in the storage chamber, wherein a negative pressure in the storage space is generated by the pump to drain lymph into the vein.

16 Claims, 3 Drawing Sheets

DEVICE FOR DRAINING LYMPH INTO VEIN

CROSS-REFERENCE TO RELATED APPLICATIONS

This application claims priority to a Taiwanese patent application no. 101145604 filed on Dec. 5, 2012.

FIELD OF INVENTION

The present invention relates to a lymph draining device, particularly to a novel lymph draining device applicable for effectively alleviating lymphedema.

DESCRIPTION OF RELATED ART

Lymphedema is a condition of tissue swelling caused by retention of a surplus of lymph. Under normal conditions, protein-enriched lymph from blood capillaries flows to lymph nodes through lymph vessels, thoracic ducts, and ultimately back to veins. However, when the lymph nodes are removed by means of surgery, and the residual lymph nodes are damaged by radiation therapy, or when the lymphatic system fails by a natural cause or when the lymphatic system is damaged due to presence of parasites, the lymph will become difficult to be recycled and is retained in the tissue, such will over time develop into lymphedema.

Breast cancer patients are generally more possible to develop upper limb lymphedema. According to statistical studies, about 6-30% of breast cancer patients presented signs of lymphedema. The reason for this is because treatment for breast cancer generally involves intervention by axillary lymph node removal and radiation, in which the surgery operation would work to remove lymphatic system in the armpit, and the residual lymphatic system undergoes fibrosis after radiation therapy. For breast cancer patients, some of them will develop signs of lymphedema in 3 years after taking radiation therapy or surgery therapy. Because lymphedema originates from excess retention of interstitial fluid having high-osmolarity proteins in the subcutaneous fat layer, the consequence of such not only shows a swelling appearance, but also becomes a breeding ground for bacteria, in worst scenarios; such can lead to skin lesions, fibrosis, and cellulitis, and can affect daily functioning and appearance.

In current time, the clinical approach to treating lymphedema mainly involves external physical pressuring, massaging, rehabilitation, in order to alleviate edema level, and through drug therapy, to prevent and cure cellulitis or lymphangitis from happening. However for patients of severe conditions of lymphedema, surgery intervention is required, for cutting off unnecessary tissue, fat, skin etc., nevertheless, such removal is not without restriction. Furthermore, there is also lymphatic venous anastomosis, but it usually returns no desired result. The generally acceptable and the most novel technology for treating four limbs lymphedema is the vascularized lymph nodes transplant operation, in which the lymph nodes at the groin of the patient is transplanted to the distal site of the limbs, for example upper limb wrists, to reconstruct the lymphatic system in the limbs, so as to treat lymphedema. Although the approach of transplanting vascularized lymph nodes can achieve the effect of treating lymphedema, such undertaking requires transplanting the lymph nodes in other parts of the body in order to achieve the therapeutic effect, and long of 6-10 hours operation and high expense of hospitalization can be improved. In addition, removing the supply portion of the lymph node can also lower lymph circulation in the donor site. In order to resolve the above problem, hereby is presented a lymph draining device that does not require transplanting the lymph nodes from other parts of the body. For patients with severe condition of lymphedema, such can decrease the likelihood of lymphedema at the transplantation site, also minimize the donor site morbidity, so as to attain the purpose of draining lymph into vein.

SUMMARY OF THE INVENTION

One main object of the present invention is to provide a device for draining lymph into vein, so as to effectively alleviate the condition of lymphedema, and lessen the discomfort caused by lymphedema.

In order to achieve the above purpose, the present invention presents a device for draining lymph into vein, comprising: a storage chamber, which comprises a chamber wall, wherein the chamber wall extends to form a storage space, and the chamber wall has at least one first opening and a second opening formed thereon; at least one osmosis membrane, which is disposed at the first opening, so as to allow the lymph to permeate into the storage space defined by the chamber wall, wherein the osmosis membrane can be made of biocompatible polymer molecules, in the present case, the osmosis membrane of the present invention can operate in two modes of design, one is to operate by electricity (which by principle involves carrying negative charge), the other is to operate without specificity oriented to electricity, in a preferred situation, the permeable membrane is made of a polymer molecule material carrying negative charge; a first conduit, of which one end is connected to the storage space of the storage chamber, and another end is connected to a vein (diameter of which is about 2-5 mm) so as to connect the storage space of the storage chamber to the vein; and a pump, which is configured in the storage chamber, wherein the pump operates to generate in the storage space of the storage chamber a negative pressure of between 10 mmHg to 30 mmHg, so that the pressure inside the storage space is less than a pressure outside the storage space (i.e. tissue gradient pressure), so as to guide the lymph shift from tissue into the inside of the storage space, and to drain the lymph into the vein through the bump and the first conduit, so as to deliver the desired effect of precluding interstitial lymph.

For the material making up the osmosis membrane, the polymer molecule material carrying negative charge of the present invention is example for such. The reason for it is because when an electrically neutral osmosis membrane is used, the fibroblast cells will attach and form a biofilm on the osmosis membrane, resulting in osmosis membrane clotted. On the other hand, when an electrically positive osmosis membrane is used, bacterial infection may cause osmosis membrane clotted due to the attachment of bacteria to the osmosis membrane. Therefore, the osmosis membrane is most preferred to be made of a polymer material carrying negative charge, in order to avoid the troublesome matter that osmosis membrane clotted causes the need for implanted device replacement by surgery. In the case where the electricity-oriented design is not adopted for the osmosis membrane, we also have other measures to fall back on. For examples, the most minimized surgical incision approach may be adopted, in which at an appropriate location, outpatient surgery is used to replace the membrane. Also suggested is local injection of drugs that can prevent the formation of obstructive membranes, such anticoagulant, fibroblast antibody, preventive or therapeutic antibiotic. In the lymph draining device of the present invention, the pump can comprise an entry terminal and an exit terminal, and the lymph permeating into the storage space of the storage chamber can drain therein from the entry terminal, out from the exit terminal, and into the vein blood vessel through the first conduit.

In one embodiment, the pump is configured inside the storage space of the storage chamber, and the exit terminal is connected to the second opening. Accordingly, the exit terminal of the pump can apply to directly guide the lymph of the storage space of the storage chamber, and lead the lymph to the second opening connected to the exit terminal, in order to drain the lymph that is outside of the device into the vein.

In another embodiment, the pump is configured outside of the storage chamber, and the entry terminal is connected to the second opening, and the exit terminal is connected to the first conduit. From this, the design of disposing the pump outside of the storage chamber can permit the pump to be detachable, and desired lymph draining pattern can be achieved as a result depending on the use of different pump subject to different demands. Even more, in order to be responsive with the lymph draining pattern for different tissues, the pump of present invention can be designed to be a pressure-adjustable pump, or a remote-controlled pump, or a wireless-controlled pump, so as to facilitate the effort to control pump pressure and speed, in order to control lymph draining.

In yet another embodiment, the pump is configured to use the battery applied in pacemaker, so as to provide long-term battery power to avoid the frequent need for having to change the battery. However, the electrical power supply for the pump is not particularly restricted, where high biocompatibility and high electrical power endurance are of prime importance for design considerations.

In still another embodiment, the pump is connected to the storage chamber through a second conduit, so that, one end of the second conduit is connected to the second opening, and another end is connected to the entry terminal of the pump. Accordingly, separating the pump and the storage chamber can make the pump detachable.

The pump of the above can be any type of micro pump, such as a micro pump, a peristaltic micro pump, or a manual micro pump, etc., but is not restricted herein.

In order to prevent the backflow of lymph during the lymph draining process in the lymph draining device of the present invention, there can further be disposed with at least one anti-reflux valve at the second opening, the first conduit, the second conduit, or a combination thereof, for the purpose of improving the draining functionality of the current invention's device.

Because the lymph draining device of the current invention can be implanted into a lymphedema-affected tissue, such as four limbs, by surgery, minimally invasive surgery, the outside of the current invention's device can be covered with a biocompatible material, or the device itself can be made of a biocompatible material to ensure no implant rejection. Any FDA approved biocompatible material is applicable, which can be selected from the group consisting of: silicone gel, silicon rubber, polytetrafluoroethylene, polyethylene, polyurethane, polydimethyl siloxane, polylactic acid, polyglycolic acid, niobium-titanium-zirconium β alloy, titanium alloy metal, gold, silver, cobalt-chromium-molybdenum alloy, and poly (hydroxyethyl methacrylate).

The lymph draining device of the current invention mainly works to allow the interstitial lymph permeate into the storage space of the storage chamber through the working of the negatively pressurized environment created inside the storage space of the storage chamber, and achieves the draining effect by the use of the pump to drain the lymph of the storage space to the vein blood vessel connected to the first conduit. Because the first conduit is connected to the vein blood vessel, the diameter of the first conduit is smaller than the vein blood vessel. Therefore, in the current invention, the diameter of the first conduit can be between 1 mm to 5 mm, and can be bound to vein blood vessel by a non-absorbable surgical wire (as shown in FIG. 3 and FIG. 4).

Further, because the size of a general protein molecule is about 20 nm, the size of a virus is about 50 nm to hundreds of nanos, the size of the bacteria is about thousands of nanos, however, albumin that is of a close relation to edema has a size of about 3.8 nm, as such, the pore of the osmosis membrane used in the device of the current invention can preferably make the lymphedema-associated protein pass through the osmosis membrane, but will keep out smallest antigens and viruses. Accordingly, pore size of the osmosis membrane of the current invention can be smaller than 50 nm, preferred to be between 10 nm to 50 nm, and more preferred to be between 20 nm to 50 nm.

In addition, the inside of the device can sometimes face the problem of clotted incurred as a result of the mixing of protein, blood cells, platelets, or any other compositions, therefore the above device of the current invention can further comprise a drug injection silicone piece on the storage chamber. Accordingly, the drug can be injected into the storage space from the drug injection silicone piece. For instance, through the protruded silicone surface, skin directed injection anti-coagulant (such as heparin), associated drugs (such as fibroblast antibody) or antibiotics, etc. can be provided, in order to keep away from coagulation and clotting inside the device, and also minimizing chances of infection.

Furthermore, in order to facilitate the process of implanting the device of the current invention into the body, the device of the current invention can be disposed on the outside surface of the storage wall of the storage chamber with at least one fixing ring. The device is preferred to be provided with 1 to 4 fixing rings, but is not particularly restricted as such. Through the fixing ring, the device can be fixed in a specific location of the tissue inside the body using non-absorbable suture. Further, the shape of the current device is not particularly limited, and a preferred shape is circular. The device size can adjust according to the demand specification. The smaller the device volume is, the better it is for the lymph draining. As such, the diameter of the preferred device can be smaller than 5 centimeters, preferred to be between 1 to 5 centimeters, and more preferred to be between 1 to 3 centimeters.

The conventional approach to alleviating lymphedema involves massaging or pressure application, but such approaches are only directed to patients of minor lymphedema. For patients with more severe conditions, preferred treatment effect could only be achievable with surgery operation. In contrast to the prior work, with the device of the current invention, effective lymph draining can be achieved by the working of the special osmosis membrane material coupled with negative pressure. Moreover, with the addition of biocompatible material covering the outside of the current device, the present invention can alleviate lymphedema through a simple surgical implant without biological rejection.

LIST OF REFERENCE NUMERALS

Figure 1:
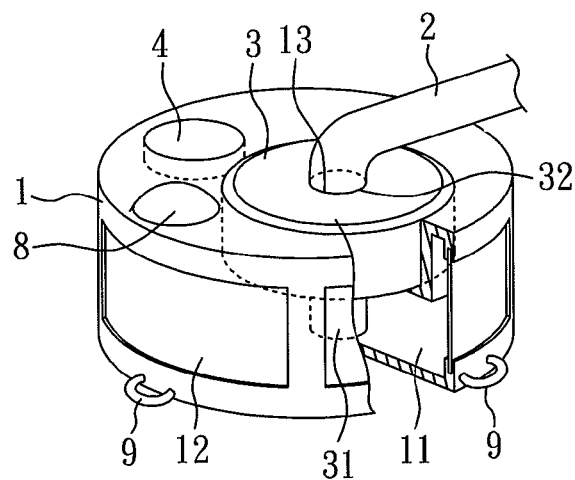
FIG. 1 shows a lymph draining device of embodiment 1 according to the present invention.

1 Storage chamber
11 Storage space
12 First opening
13 Second opening
2 First conduit
21 Groove
3 Pump
31 Entry terminal
32 Exit terminal
4 Power supply
5 Anti-reflux valve
6 Second conduit
7 Blood vessel
8 Drug injection silicone piece
9 Fixing ring

DETAILED DESCRIPTION OF THE PREFERRED EMBODIMENT

Hereafter, examples will be provided to illustrate the embodiments of the present invention. Other advantages and effects of the invention will become more apparent from the disclosure of the present invention. Other various aspects also may be practiced or applied in the invention, and various modifications and variations can be made without departing from the spirit of the invention based on various concepts and applications.

Embodiment 1

FIG. 1 is a lymph draining device of embodiment 1 according to the present invention. The lymph draining device of the current embodiment comprises: a storage chamber 1, comprising a chamber wall, wherein the chamber wall extends to form a storage space 11, and there is formed on the chamber wall a plurality of first openings 12 and a second opening 13, also on the outside of the chamber wall there is disposed two fixing rings 9; at least one osmosis membrane, which is disposed at the first opening 12, wherein the osmosis membrane of the current embodiment circles around the storage chamber 1, so as let the lymph to effectively pass through the osmosis membrane and enter into the storage space 11. A first conduit 2, of which one end is connected to the storage space 11 through the second opening 13, and another end is connected to a blood vessel (not shown in the FIG. 2), so that the storage space 11 of the storage groove 1 is connected to the blood vessel; in this case, the blood vessel is vein. A pump 3, which is configured in the storage chamber 1, wherein the pump 3 operates to generate a negative pressure of 10 to 30 mmHg to make a pressure gradient inside the storage space 11, which is less than a pressure outside the storage space 11, so as to guide the lymph from outside into the inside of the storage space 11, and to introduce the lymph into the blood vessel through the first conduit 2, so as to preclude the lymph.

For the current device, there further comprises a drug injection silicone piece 8, by which anticoagulant, antibody or antibiotic can be injected into the storage space 11. Preferably, the diameter of the drug injection silicone piece is 1 to 3 cm; however, it does not be limited thereto.

In the current embodiment, the pump 3 is a micro pump, which is configured in the storage space 11 of the storage chamber, and the exit terminal 32 is connected to the second opening 13. As such, the exit terminal 31 of the pump can directly guide the lymph of the storage space 11, and thereby guide the lymph to the second opening 13 connected to the exit terminal 32, so as to drain the lymph that is outside of the device to the vein. Moreover, the current invention is further disposed with a power supply 4, which works to supply the pump 3 with electrical battery power for running the operation.

Figure 2:
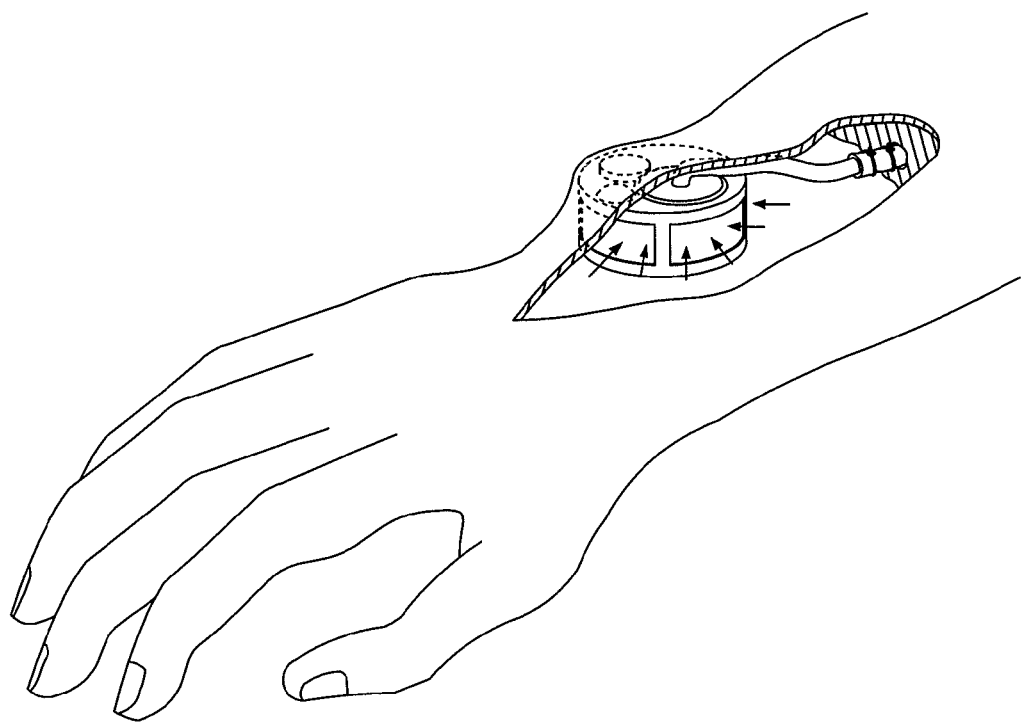
FIG. 2 shows the installation of the lymph draining device of embodiment 1 according to the present invention.
Figure 3:
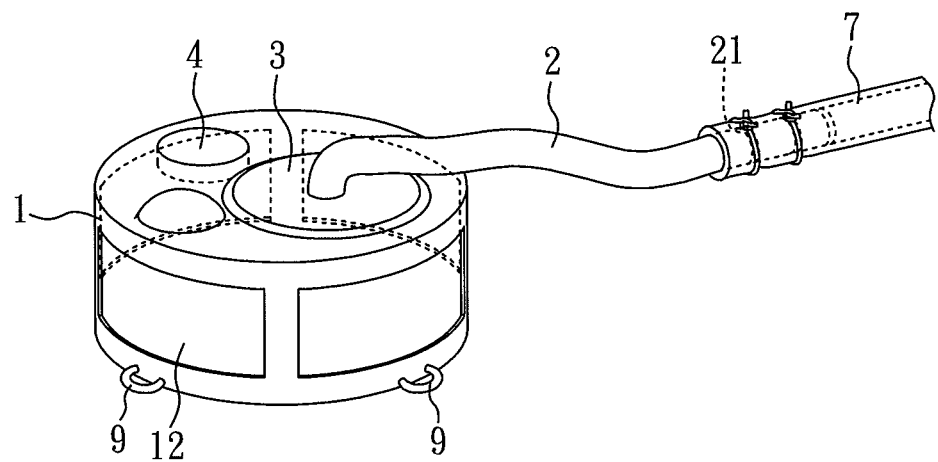
FIG. 3 shows a partial view of the lymph draining device of embodiment 1 according to the present invention.

In addition, the pore diameter of the osmosis membrane of the current device is 20-50 nm, to allow lymph to permeate into the storage chamber. The outside of the current device is covered with a material of biocompatible silicone gel, as such, the lymph draining device can be implanted into the subcutaneous tissue, in order to alleviate pain and irritation. FIG. 2 shows the installation of the lymph draining device of embodiment 1 according to the present invention. Through the negative pressure generated by the micro pump in the storage chamber of the current device, the lymph can permeate into the space, then, through the pump's draining, the lymph drains into the vein through the first conduit. FIG. 3 shows a partial view of the lymph draining device of embodiment 1 according to the present invention. In this illustration, the manner by which the first conduit 2 is connected to the blood vessel 7 is through the grooves 21 of the other end of the first conduit 2, to be connected to the blood vessel 7, and the first conduit 2 is fixed to the blood vessel 7 through a non-absorbance suture. Accordingly, the device of the present embodiment can drain lymph permeating from the current device into blood vessel.

Embodiment 2

Figure 4:
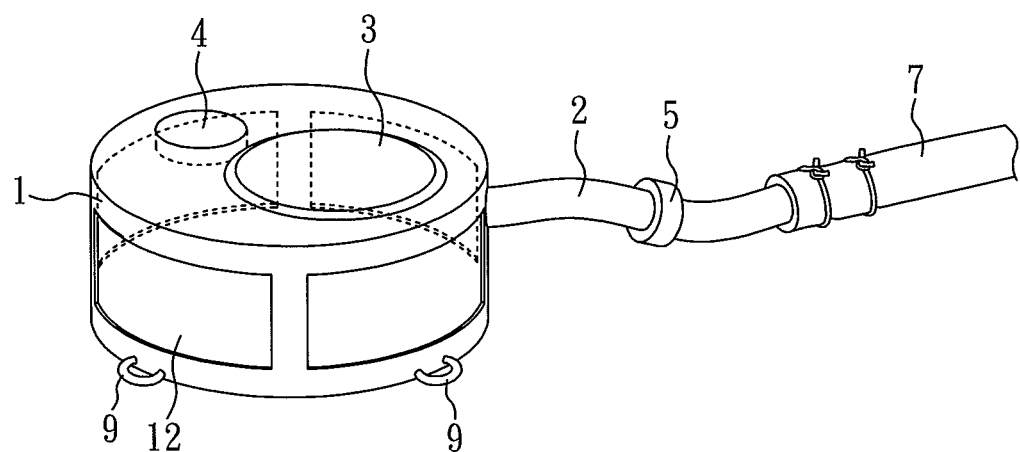
FIG. 4 shows a lymph draining device of embodiment 2 according to the present invention.

As shown in FIG. 4, the FIG. 4 is a lymph draining device of embodiment 2 according to the present invention. The current embodiment is generally the same as embodiment 1, except that the first conduit 2 is disposed on the lateral sides of the storage chamber 1, and the current device is disposed with an anti-reflux valve 5. The valve has a quasi-valve functionality, to prevent the lymph from back flowing into the storage chamber, and favorably affect the lymph draining efficiency. Here, the material of the anti-reflux valve is made of an elastic material of silicone, which is biocompatible. In addition, the current invention does not have a drug injection silicone piece.

Embodiment 3

Figure 5:
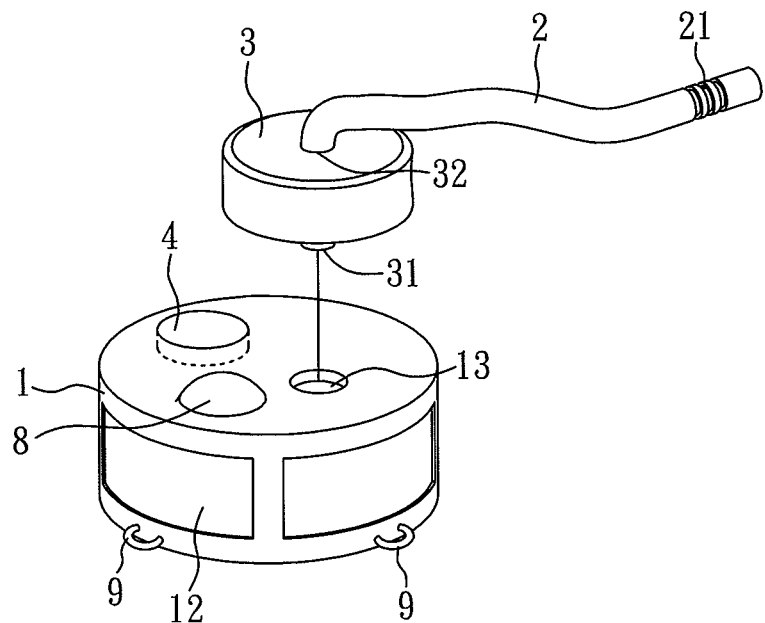
FIG. 5 is a lymph draining device of embodiment 3 according to the present invention.

Referring now to FIG. 5, FIG. 5 shows a lymph draining device of embodiment 3 according to the present invention. The current embodiment is generally the same as embodiment 1, except the disposition of the pump 3.

The pump 3 of embodiment 1 is disposed inside the storage chamber. However, the pump 3 of the current embodiment is disposed outside of the storage chamber 1, and is closely connected to the outer wall of the storage chamber 1. In this embodiment, the pump 3 is illustrated as a peristaltic micro pump. The entry terminal 31 of the pump is connected to the second opening 13, and the exit terminal 32 is connected to the first conduit 2. As such, by the design of disposing the pump 3 outside of the storage chamber 1, the pump 3 is configured to be detachable, and the use of the pump 3 can adjust depending on different demand specification, for the purpose of achieving preferred lymph draining. For example, the pump 3 of the current embodiment can be designed to be mediated by remote control, Bluetooth or radio frequency, and the speed by which interstitial lymph drains to vein can be tuned by the output power and speed of the pump 3.

Embodiment 4

Figure 6:
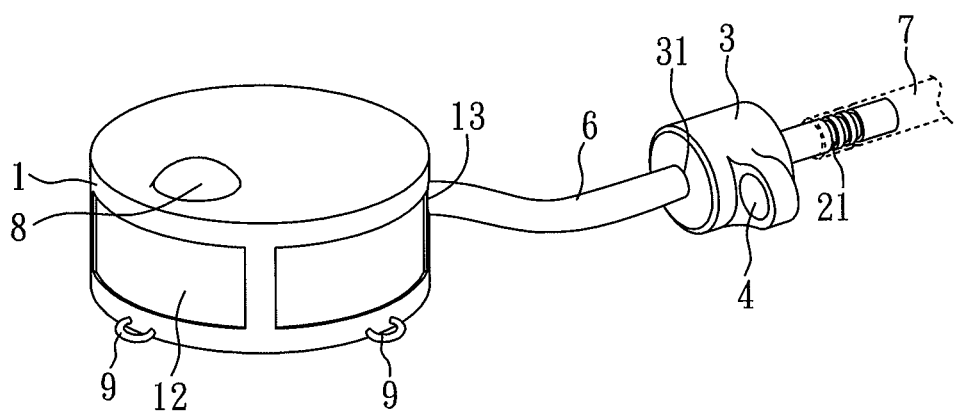
FIG. 6 is a lymph draining device of embodiment 4 according to the present invention.

As shown in FIG. 6, FIG. 6 is a lymph draining device of embodiment 4 according to the present invention. The present embodiment is generally the same as the embodiment 3, except the location of the pump 3 and the first conduit 2.

The pump 3 of embodiment 3 is tightly disposed on the outside surface of the storage chamber. However, the pump 3 of the current embodiment has a second conduit 6, a terminal of which is connected to the second opening 13, and the other end is connected to the entry terminal 31 of the pump 3. Accordingly, the pump 3 is enabled to be detachable through separating the pump 3 away from the storage chamber 1.

Because of the detachable design for pump 3 of the current embodiment, the pump 3 can be connected in series depending on different demand specification, so as to create the negative pressure needed for the storage space 11 of the storage chamber 1, to facilitate lymph draining. In addition, it is even operable to set the detachable pump 3 to be a manual micro pump. Accordingly, in addition to electrically driving the pump 3, the pump can even be powered by a manual mechanism, to give the pump 3 a driving force. Further, the first conduit 2 of the current invention is disposed on the lateral sides of the storage chamber 1, so as to decrease the discomfort at the lymphedema location on the patient created by the implant of the current device.

The above embodiments are for the purpose of better describing the current invention and are of exemplary nature only. The scope of right asserted by the current invention is based on the scope of claims in this application, and is not intended to be restricted by the above embodiments.

What is claimed is:

1. A device for draining lymph into vein, comprising:
   a storage chamber, comprising a chamber wall, wherein the chamber wall extends to form a storage space, and the chamber wall has a plurality of first openings that circle around the chamber wall and a second opening formed thereon;
   a plurality of osmosis membranes, which are made of a negatively charged polymer molecule material, the osmosis membranes circle around the chamber wall and are configured at the first openings to allow lymph to permeate into the storage space of the storage chamber solely via the osmosis membranes, wherein a pore diameter of the osmosis membrane is between 20 nm to 50 nm;
   a first conduit, of which one end is connected to the storage space of the storage chamber via the second opening, and another end is adapted to be connected to a vein, so as to allow the storage space of the storage chamber to connect to the vein; and
   a pump, which is configured in the storage chamber, wherein the pump operates to generate a negative pressure to make a pressure inside the storage space smaller than a pressure outside the storage space, the device being thereby configured to guide the lymph from outside the storage space into the inside of the storage space, and to drain the lymph into the vein through the first conduit;
   wherein the device for draining lymph into vein is adapted to be implanted in a subcutaneous fat layer;
   wherein the diameter of the device is between 1 to 5 centimeters.

2. The device of claim 1, wherein the pump comprises an entry terminal and an exit terminal, the lymph permeating into the storage space of the storage chamber drains from the entry terminal to the exit terminal, and drains into the vein through the first conduit.

3. The device of claim 2, wherein the pump is configured in the storage space of the storage chamber, and the exit terminal is connected to the second opening.

4. The device of claim 2, wherein the pump is configured on an outside of the storage chamber, and the entry terminal is connected to the second opening, and the exit terminal is connected to the first conduit.

5. The device of claim 4, wherein the pump further comprises a second conduit, and the entry terminal is connected to the second opening through the second conduit.

6. The device of claim 4, wherein the pump is a detachable pump.

7. The device of claim 5, wherein the pump is a detachable pump.

8. The device of claim 1, wherein the pump is a micro pump, a peristaltic micro pump, or a manual micro pump.

9. The device of claim 5, further comprising an anti-reflux valve, which is configured at the second opening, the first conduit, the second conduit, or a combination thereof.

10. The device of claim 1, wherein a biocompatible material covers the periphery of the lymph draining device.

11. The device of claim 10, wherein the biocompatible material is one selected from the group consisting of: silicone, silicone rubber, polyethylene, polytetrafluoroethylene, polyurethane, polydimethyl siloxane, polylactic acid, polyglycolic acid, niobium-titanium-zirconium β alloy, titanium alloy metal, gold, silver, cobalt-chromium-molybdenum alloy, and poly (hydroxyethyl methacrylate).

12. The device of claim 1, wherein a diameter of the first conduit is between 1 mm to 5 mm.

13. The device of claim 1, wherein the negative pressure generated by the pump in the storage space is between 10 mmHg to 30 mmHg.

14. The device of claim 1, further comprising a drug injection silicone piece, which is configured on the storage chamber to allow a drug to be injected into the storage space of the storage chamber through the drug injection silicone piece.

15. The device of claim 1, further comprising at least one fixing ring, wherein the fixing ring is configured on an outside of the storage wall of the storage chamber.

16. The device of claim 1, wherein the device is configured to allow lymph to permeate directly into the storage space of the storage chamber after passing only through the plurality of first openings and the osmosis membranes.

* * * * *